(12) United States Patent
Peel, III, deceased et al.

(10) Patent No.: US 6,662,130 B1
(45) Date of Patent: Dec. 9, 2003

(54) SYSTEMS AND METHODS FOR CALIBRATING A DISTORTED SIGNAL WITH ANOTHER SIGNAL OF KNOWN CALIBRATION

(75) Inventors: Harry Herbert Peel, III, deceased, late of San Antonio, TX (US), by Kimesha May Angell Peel, Independent Executrix; Keith Alan Bartels, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 10/167,448

(22) Filed: Jun. 13, 2002

(51) Int. Cl.[7] ............... A61B 5/62; G01N 29/00; G06F 19/00

(52) U.S. Cl. ............... 702/104; 600/485; 600/494; 73/579

(58) Field of Search .................. 702/104, 66; 600/485, 600/494, 500; 73/579, 602, 622

(56) References Cited

U.S. PATENT DOCUMENTS

| | | | | | |
|---|---|---|---|---|---|
| 4,617,937 | A | * | 10/1986 | Peel et al. | 600/493 |
| 4,779,626 | A | * | 10/1988 | Peel et al. | 600/488 |
| 5,165,416 | A | * | 11/1992 | Shinoda et al. | 600/485 |

* cited by examiner

*Primary Examiner*—Kamini Shah
(74) *Attorney, Agent, or Firm*—Oliff & Berridge, PLC

(57) ABSTRACT

An uncalibrated sensor located at a first location relative to a physical phenomenon is calibrated using a calibrated sensor spaced away from the uncalibrated sensor at a second location relative to the physical phenomenon and a frequency-domain transfer function that relates the physical phenomenon at the second location to the output of the uncalibrated sensor.

18 Claims, 10 Drawing Sheets

Brachial Blood Pressure

Radial Blood Pressure

SYSTEMS AND METHODS FOR CALIBRATING A DISTORTED SIGNAL WITH ANOTHER SIGNAL OF KNOWN CALIBRATION

BACKGROUND OF THE INVENTION

1. Field of the Invention

This invention relates to systems and methods for calibrating an uncalibrated measuring device.

2. Description of Related Art

Sensors, or more generally, transducers, are used in many disciplines to sense a physical phenomenon and to generate an output signal based on the sensed physical phenomenon. Commonly, such sensors or transducers are calibrated based on known simultaneous measurements of the physical phenomenon. In practice, the output signal from the sensor or transducer is calibrated using a measurement of the physical phenomenon made with another instrument. In general, this second instrument has been calibrated itself by some agreed-upon method and against a specified physical object, physical phenomenon, and/or standard.

In some types of measurements, the sensor or transducer of a measurement device cannot be directly coupled to the physical phenomenon to be measured using that sensor or transducer. Such indirect measurements are dependent upon the coupling of the sensor or transducer to the system in which the physical phenomenon being measured occurs. In this case, calibrating the sensor or transducer is dependent both upon the measurement characteristics of the sensor or transducer and upon the coupling of the sensor or transducer to the system being measured. As a result, indirect measurements often require calibrating the sensor or transducer to additional measurements of the system after the sensor or transducer is connected to the system.

SUMMARY OF THE INVENTION

However, when attempting to calibrate a sensor or transducer that makes indirect measurements, it is often difficult, if not impossible, to make, at the same location on the system, both the calibration measurements using that sensor or transducer required to calibrate that sensor or transducer and to make the second set of measurements necessary for calibrating such indirect measurements. This typically, although not always, occurs due to the size of the sensors relative to the system being measured and the practical limitations when making measurements on the system being measured.

For example, due to the size of the sensor or transducer, the size of the secondary measurement device and/or the practical limitations of making blood pressure measurements on living beings, it is generally impossible to measure the blood pressure of a blood vessel within a living being using the sensor or transducer to be calibrated, while making the secondary measurements (discussed above) at the same point on the blood vessel using a second measurement device. For example, the known blood pressure measurements, which are used as the "additional measurements" for calibrating indirect measurements, are typically obtained from a human being by placing a cuff over the brachial artery of the upper arm. In contrast, a tonometric sensor to be calibrated is placed against the radial artery at the wrist of the human being. Moreover, the blood pressure cuff will very often be placed on an opposite limb from that on which the blood pressure of the human being is being measured using the tonometric sensor. However, it should be appreciated that this inability to make measurements at the same location relative to the system due to physical constraints is not restricted to measuring blood pressure in a living being.

It should also be appreciated that, if the calibration of the sensor or transducer is to be accurate, it is usually necessary that the sensor or transducer being calibrated be exposed to the identical level of the physical phenomenon as that to which the standard measurement device is exposed. If these physical phenomenon cannot be measured both by the sensor or transducer to be calibrated and by the standard measurement device at the same point and if the values of the physical phenomenon are not the same at the two measurement locations, an error in the calibration can result. The values of the physical phenomenon at the two measurement points can differ due to a time delay of the propagation of the physical phenomenon between the two measurement locations and/or due to a distortion of the physical phenomenon between the two measurement locations.

For example, the physical phenomenon of blood pressure in a vascular system of a living being experiences both of these error-inducing characteristics. That is, the propagation of the blood pressure pulse wave through the vascular system has a finite velocity. As a result, the blood pressure measured at a second, downstream location of the vascular system is delayed in time from the blood pressure that occurs at a first, upstream, measurement location of the vascular system. At the same time, as the blood pressure pulse wave propagates through the vascular system, the physiological characteristics of the vascular system of the living being produces distortions in the blood pressure pulse wave that makes the blood pressure pulse wave take different shapes at the first and second measurement locations.

This invention provides systems and methods for calibrating a sensor or transducer that is indirectly coupled to a phenomenon occurring within a system.

This invention separately provides systems and methods for calibrating sensors or transducers that are indirectly coupled to a system where the secondary measurement occurs at a location separated from the location of the measurements obtained by the sensor or transducer to be calibrated.

This invention separately provides systems and methods for calibrating a sensor or transducer relative to a physical phenomenon that is distorted relative to a measurement of that physical phenomenon by a device of known calibration.

This invention separately provides systems and methods for calibrating a sensor or transducer that is indirectly coupled to a physical phenomenon occurring within a living being.

This invention separately provides systems and methods for calibrating a blood pressure transducer that generates an electric signal from a blood pressure signal occurring within a living being.

This invention separately provides systems and methods for calibrating a blood pressure sensor or transducer that senses a blood pressure signal in a living being relative to a separate measurement of the blood pressure signal within the living being taken at a point separated from the location of the blood pressure sensor or transducer to be calibrated.

This invention separately provides systems and methods for determining the calibration parameters of an uncalibrated device in situ using frequency analysis of the naturally occurring variations of the system being sensed using the uncalibrated device.

In various exemplary embodiments of the systems and methods according to this invention, a first transfer function that defines the transformation of a physical phenomenon between a first location and a second location is defined. Next, a value of that transfer function at a particular frequency is determined. Independently, a second transfer function, defining the conversion of the input physical phenomenon to the output signal generated by the sensor or transducer to be calibrated in response to measuring that physical phenomenon, is defined. Additionally, a relationship between the first transfer function and the second transfer function is also defined. The relationship between these two transfer functions is the reciprocal of a calibration coefficient needed to calibrate the uncalibrated sensor or transducer. By obtaining a value for each of the two transfer functions at a particular time, a particular frequency or the like, the calibration coefficient can be obtained.

Independently, the output of the uncalibrated sensor or transducer is based on the calibration coefficient, the input physical phenomenon and a calibration constant. Because the calibration coefficient is known, and because the input and output signal values can be determined or derived, the calibration constant can be determined. By determining the calibration coefficient and calibration constant for the uncalibrated sensor or transducer in situ using frequency analysis of the naturally occurring variations of the system, inaccuracies occurring as a result of using existing time-domain calibration methods can be reduced, or ideally, eliminated.

These and other features and advantages of this invention are described in, or are apparent from, the following detailed description of various exemplary embodiments of the systems and methods according to this invention.

BRIEF DESCRIPTION OF THE DRAWINGS

Various exemplary embodiments of this invention will be described in detail, with reference to the following figures, wherein.

DETAILED DESCRIPTION OF EXEMPLARY EMBODIMENTS

Figure 1:
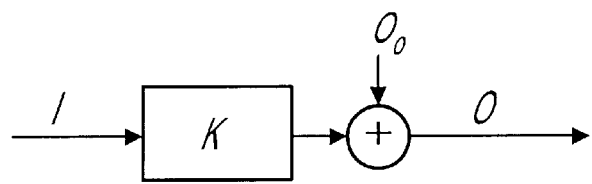
FIG. 1 is a schematic diagram of one exemplary embodiment of an uncalibrated device that measures physical phenomenon.

As described herein, this invention provides systems and methods for calibrating a first signal obtained at a first location relative to a system with a second signal of known calibration obtained at a second location relative to the system when the phenomenon being measured has different characteristics at the two locations. Moreover, this invention provides systems and methods that adjust the coefficients of the calibration equation such that distortions in the phenomenon between the first and second locations are compensated for. These distortions may make simultaneously-measured values in each signal different due to the differences in the physical phenomenon that occurs at the first and second measurement locations.

It should be appreciated that, in the following detailed discussion, the systems and methods according to this invention may be described relative to calibrating an arterial pressure tonometer using a calibrated non-invasive blood pressure monitor employing an air-filled occlusion cuff. However, it should be appreciated that the systems and methods of this invention are not limited to calibrating an uncalibrated arterial pressure tonometer relative to a previously-calibrated occlusion cuff blood pressure monitor. Rather, the systems and methods of this invention can be used to calibrate any uncalibrated sensor or transducer to a system to be measured, when a calibrated device used in the calibration process measures the system at a location separate from the location of the system measured by the uncalibrated sensor or transducer.

A signal generated by measuring some phenomenon of a system using a first device is generally calibrated by comparing signals representing simultaneous measurements of the phenomenon by the first device and a second, previously-calibrated device. In practice, an uncalibrated device is usually calibrated by measuring a physical phenomenon with a calibrated measuring device that has been calibrated by some agreed-upon method and against a specified standard to generate a calibrated signal. The calibrated signal of the phenomenon generated by the calibrated device is then compared to an uncalibrated signal measuring the same phenomenon generated by an uncalibrated measuring device.

In some types of measurements, the sensor or transducer of the measuring device, whether calibrated or uncalibrated, cannot directly measure the phenomenon to be measured. For example, the transmural pressure changes of a blood vessel may not be directly measured by measuring a pressure across the walls of a blood vessel. Instead, an indirect measurement may be used to measure a blood pressure pulse wave that is transmitted from the blood vessel to the surface of the skin that overlies the blood vessel. For indirect measurements, calibrating an uncalibrated device depends both on the measurement characteristics of the sensor or transducer of the measuring device and on the coupling of the sensor or transducer of the measuring device to the phenomenon being measured. As a result, indirect measurements often require the uncalibrated measuring device be calibrated to a calibrated signal after the uncalibrated measuring device is indirectly coupled to the phenomenon being measured.

A calibration process may include simultaneously measuring the phenomenon using an uncalibrated measuring device and using a calibrated measuring device to obtain two or more generally simultaneous values of the phenomenon for the two devices. It should be appreciated that "generally simultaneous" encompasses both measurements that are roughly contemporaneous, such that the same input signal, within the propagation delay, is measured at each of the two locations. However, this term also encompasses measurements taken at two different times, which could be separated by minutes, hours, or even days, so long as a number of conditions are met.

In particular, the two measurements can be separated by any interval so long as the system which is being measured has not significantly changed between the two measurements. For example, many real-life dynamic mechanical, hydraulic, pneumatic, electrical, and chemical systems experience aging, wear and the like that cause the long-term dynamic response of such systems to change and/or drift. Such systems can also experience inputs that cause long-term changes to the dynamic response of such systems. That is, such systems are generally stable over some limited time interval, but change over longer intervals. It should be appreciated that, as long as the two measurements are made within the time interval over which the system being measured is stable, those two measurements are "roughly simultaneous".

A mathematical relationship may then be produced that relates the measured signal levels obtained by the uncalibrated measuring device to the measured signal levels obtained by the calibrated measuring device. For an uncalibrated measuring device that transduces an input signal into an output signal by scaling and shifting, this transduction can be represented as:

$$O = KI + O_0, \tag{1}$$

where:
- O is the resultant output signal;
- K is a constant of proportionality;
- I is the input signal; and
- $O_0$ is a constant equal to the output signal for an input signal having a value of zero.

FIG. 1 is a schematic diagram that implements Eq. (1) for an input signal I representing a pressure and an output signal O representing a voltage. In various exemplary embodiments, the input signal is, for example, a blood pressure within a blood vessel, while the output signal is a voltage representing the force or pressure applied against a pressure-to-voltage sensor or transducer by the skin of a living being in response to the blood pressure in the blood vessel.

A linear equation can be used to calibrate such an uncalibrated measuring device. One such linear equation is:

$$I = C_c O + I_0, \tag{2}$$

where:
- I is the input signal against which the output signal is to be calibrated;
- $C_c$ is a calibration coefficient;
- O is the output signal to be calibrated to the input signal; and
- $I_0$ is a calibration constant.

Figure 2:
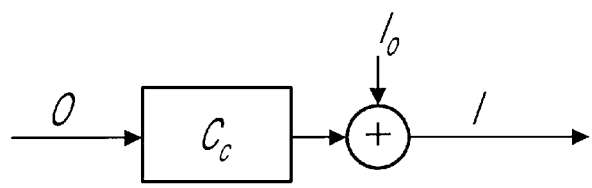
FIG. 2 is a schematic diagram of one exemplary embodiment of a system usable to calibrate the uncalibrated device shown in FIG. 1.

As shown in FIG. 2, which corresponds to Eq. (2), in the case of a pressure-to-voltage transducer, the calibration constant $I_0$ is an offset pressure $P_0$. In various exemplary embodiments, where the input signal is the blood pressure P within a blood vessel, the value of the offset pressure $P_0$, is the blood pressure when the value of a measured electrical signal E is zero.

The input signal can be measured using a calibrated device that is able to monitor the input signal. The output signal can be generated by an uncalibrated transducer that converts the input signal to the output signal. In this case, if simultaneous measurements of the input signal and the output signal are made for two different values of the input signal, then the calibration coefficient $C_c$ is:

$$C_C = \frac{1}{K} = \frac{I_B - I_A}{O_B - O_A}; \tag{3}$$

where:
- K is the constant of proportionality (from Eq. (1));
- $I_A$ is a first calibrated input measurement;
- $I_B$ is a second calibrated input measurement;
- $O_A$ is a first uncalibrated output measurement corresponding to the first calibrated input measurement $I_A$; and
- $O_B$ is a second uncalibrated output measurement corresponding to the second calibrated input measurement $I_B$.

The calibration constant $I_0$ can then be determined by using the calibration coefficient $C_c$ and the measured input signals and the measured output signals. In particular, given the value for the calibration coefficient $C_c$, determined using Eq. (3) and the values for the input signal and the output signal used in Eq. (3), Eq. (2) can be rewritten as:

$$I_0 = I_A - C_c O_A = I_B - C_c O_B. \quad (4)$$

In some cases, when a coupling of the uncalibrated measuring device to the system cannot be readily adjusted, the uncalibrated measuring device must be calibrated after it is coupled to that system. In such systems that measure a time-varying phenomenon, such as, for example, blood pressure, the time variation in the measured phenomenon can be used for calibration purposes. The input signal obtained by sensing a time-varying phenomenon, such as blood pressure, includes a constant average component and a time-varying component. Thus, the total measured value of the input signal is:

$$I(t) = \bar{I} + i(t), \quad (5)$$

where:

$I(t)$ is the total measured value of the input signal;

$\bar{I}$ is the constant average component of the input signal; and $i(t)$ is the time-varying component of the input signal.

For a transducer that converts an input signal into an output signal, a time-varying output signal generated in response to a time-vary input signal can also be represented by a constant average output component and a time-varying output component. Accordingly, based on Eq. (5), Eq. (2) can be rewritten as:

$$I(t) = C_c O(t) + I_0 = C_c \bar{O} + C_c o(t) + I_0. \quad (6)$$

where:

$I(t)$ is the total measured value of the input signal;

$C_c$ is the calibration coefficient;

$O(t)$ is the total measured value of the output signal;

$\bar{O}$ is the constant average component of the output signal; and $o(t)$ is the time-varying component of the output signal.

If $I(t)$ and $O(t)$ are periodic functions with equal periods, then the constant average component of the input signal is:

$$\bar{I} = \frac{1}{T} \int_{t_0}^{t_0 + kT} I(t) dt, \quad (7)$$

and the constant average component of the output signal is:

$$\bar{O} = \frac{1}{T} \int_{t_0}^{t_0 + kT} O(t) dt, \quad (8)$$

where:

$t_0$ is an arbitrary time;

k is a non-zero integer; and

T is the period of the time varying periodic functions $I(t)$ and $O(t)$.

Eq. (6) can be used in two ways to calibrate the output signal in terms of the input signal. First, two time-varying input signals $I_1(t)$ and $I_2(t)$, and the corresponding time-varying output signals $O_1(t)$ and $O_2(t)$, can be measured over different time periods. Then, provided that the two time-varying input signals $I_1(t)$ and $I_2(t)$ have different values for the average component, the calibration coefficient $C_c$ is:

$$C_C = \frac{\bar{I}_2 - \bar{I}_1}{\bar{O}_2 - \bar{O}_1}, \quad (9)$$

where:

$\bar{I}_1$ is the constant average component of the first time-varying input signal $I_1(t)$;

$\bar{I}_2$ is the constant average component of the second time-varying input signal $I_2(t)$ and $(\bar{I}_1 \neq \bar{I}_2)$;

$\bar{O}_1$ is the constant average component of the first output signal $\bar{O}_1(t)$ obtained based on the first input signal $I_1(t)$; and $\bar{O}_2$ is the constant average component of the second output signal $O_2(t)$ obtained based on the first input signal $I_2(t)$ and $\bar{O}_1 \neq \bar{O}_2$.

Alternatively, the time-varying input signal $I(t)$ and the corresponding output signal $O(t)$ can be measured at two distinct times $t_1$ and $t_2$. Then, provided that the time-varying output signal $O(t)$ has different values for the time-varying component $o(t)$ at the two times $t_1$ and $t_2$, the calibration coefficient $C_c$ is:

$$C_C = \frac{I(t_2) - I(t_1)}{O(t_2) - O(t_1)} = \frac{\bar{I} + i(t_2) - \bar{I} - i(t_1)}{\bar{O} + o(t_2) - \bar{O} - o(t_1)} = \frac{i(t_2) - i(t_1)}{o(t_2) - o(t_1)}, \quad (10)$$

where:

$I(t_1)$ and $I(t_2)$ are the values of the time-varying input signal $I(t)$ at the first and second times $t_1$ and $t_2$;

$O(t_1)$ and $O(t_2)$ are the values of the time-varying output signal $0(t)$ at the first and second times $t_1$ and $t_2$;

$\bar{I}$ is the constant average component of the time-varying input signal $\bar{O}$ is the constant average component of the electrical signal $O(t)$ obtained based on the input signal $I(t)$;

$i(t_1)$ and $(t_2)$ are the values of the time-varying component of the time-varying input signal $I(t)$ at the first and second times $t_1$ and $t_2$; and $o(t_1))$ and $o(t_2)$ are the values of the time-varying component of the time-varying output signal $O(t)$ at the first and second times $t_1$ and $t_2$ and $o(t_2) \neq o(t_1)$.

Sometimes, it is not possible to measure the value of a phenomenon using a calibrated device at the same location where an uncalibrated sensor or transducer, that converts the value of a phenomenon to an output signal, is placed. For example, it is often impossible to measure the blood pressure of a living being using a calibrated blood pressure monitor at the same anatomical site on the living being where an electrical transducer is placed that converts the sensed blood pressure to an electrical signal. Typically, the calibrated blood pressure measurement is made using an air-filled occlusive cuff placed over the brachial artery of a forelimb of the living being, while an uncalibrated tonometer, which produces electrical signals in response to pressure changes, may be placed over the radial artery of the living being near the end of that forelimb of the living being. Often, the blood pressure cuff may be placed on a forelimb opposite to the forelimb on which the tonometer is placed.

Desirably, if the calibration is to be accurate, the uncalibrated device should measure the same physical phenomenon as that measured by the calibrated measuring device. When the calibrated device and the uncalibrated device are placed at two spatially separated locations, such as when the uncalibrated blood pressure measuring device and the calibrated blood pressure measuring device cannot make measurements at the same anatomical site, an error in calibration can result if the phenomenon being sensed, such as the blood pressure, is not the same at the two locations. The two measures of the phenomenon will differ if there is a time delay between the occurrence of the phenomenon between the two locations or there exists a distortion of the phenomenon that occurs at the location of the uncalibrated device with respect to phenomenon that occurs at the location of the calibrated device, or both.

Figure 3:
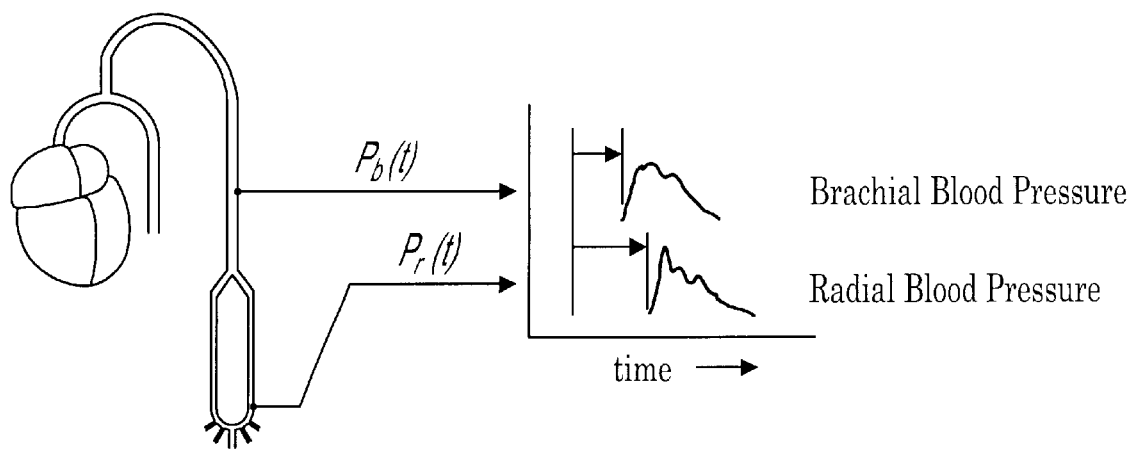
FIG. 3 illustrates differences in the blood pressure signals and the time delays between different sites in a vascular system of a living being.

For example, as shown in FIG. 3, in a living being, the blood flows from the heart to the smaller arterial branches of the living being's vascular system. The blood pressure pulse wave, originating due to the pulsatile contractions of the heart, has a finite propagation velocity through the vascular system. Thus, the waveform of the blood pressure pulse wave sensed at the radial artery is delayed relative to the blood pressure pulse wave sensed at the brachial artery. Additionally, as shown in FIG. 3, as the blood pressure pulse wave propagates through the arterial branches, a distortion in the pulse waveform occurs that makes the shapes of the blood pressure pulse waveforms different when measured at the brachial artery and at the radial artery.

When the blood pressure of the living being is measured at other locations or sites of the living being, the distortion in the shape of the pulse waveform locations may be negligible or non-existent. The blood pressure pulse waveforms may then be assumed to be the same shape at these locations, except for a possible time delay. However, any time delay precludes using pressure measurements $P(t_1)$ and $P(t_2)$ and the obtained electrical signal measurements $E(t_1)$ and $E(t_2)$ as the input and output signals $I(t)$ and $O(t)$, respectively, to determine the calibration coefficient using Eq. (10). When there is a time delay between measuring locations in the phenomenon as it occurs at those measuring locations, the time-varying signals may be shifted relative to each other, such that characteristic features, for example, maxima and minima, of the time-varying signal may be used as values by which a calibration coefficient may be obtained using Eq. (10).

Figure 4:
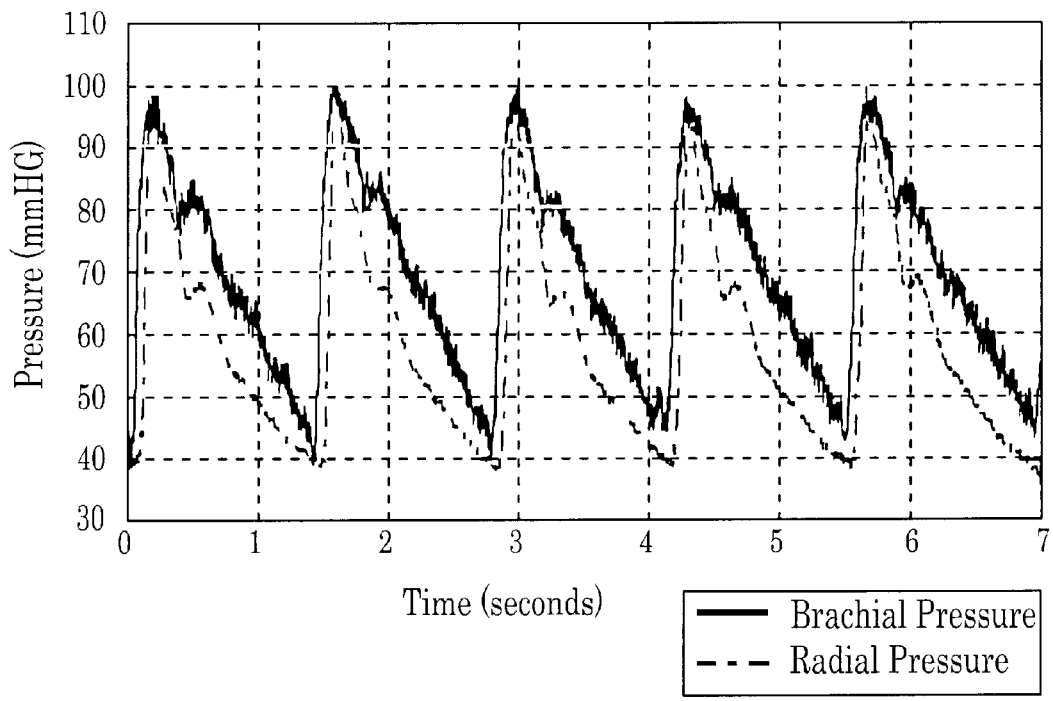
FIG. 4 is a graph plotting a signal generated by measuring a physical phenomenon at one position in a system and a second signal generated by measuring the physical phenomenon at a second position in the system, where the second signal is calibrated by matching the maximum and minimum of the second signal to the maximum and minimum of the first signal.

A tonometer placed over the radial artery of a living being has been calibrated assuming that the distortion is negligible. FIG. 4 shows a brachial artery blood pressure pulse waveform, shown by the solid line, measured by a calibrated blood pressure monitor. The radial artery blood pressure pulse waveform is shown by the dotted line and was measured by a tonometer that is calibrated by matching the maximum and the minimum of the two waveforms. However, the obvious difference in the shapes of the two waveforms of FIG. 4 demonstrates that the distortion measured at the radial artery is not negligible.

As shown in FIG. 3, the amplitude of the time-varying (AC) components of the blood pressure signal at the radial artery differs greatly from that the brachial artery due to the pulse transmission characteristics of the vascular system. As shown in FIG. 4, distortion, that is, a change in shape of the blood pressure signal at the radial artery relative to the brachial artery, is characteristic of the blood pressure pulse transmission. A technique that matches features of the two blood pressure signals, such as, peak amplitudes, which are used in the calibration process shown in FIG. 4, is not sufficient for accurate calibration.

The changes in a physical phenomenon between a first measurement location "a" of a system and a second measurement location "b" of the system can be described by a frequency-domain transfer function $\hat{H}(f)$:

$$\hat{H}_{ab}(f) = \frac{\hat{I}_2(f)}{\hat{I}_1(f)}, \tag{11}$$

where:
$\hat{H}_{ab}(f)$ is the frequency-domain transfer function of the input signal between the first measurement location "a" and the second measurement location "b";
$\hat{I}_1(f)$ is the Fourier transform of the first time-varying input signal $I_1(t)$ measured at the first measurement location "a"; and
$\hat{I}_2(f)$ is the Fourier transform of the second time-varying input signal $I_2(t)$ measured at the second measurement location "b".

Eq. (11) can be reformulated to represent the changes in a blood pressure pulse wave of a living being as the blood pressure pulse wave travels from a brachial artery of the living being to a radial artery of the living being. In particular, the changes can be described in terms of an arterial pressure transfer function:

$$\hat{H}_{br}(f) = \frac{\hat{P}_b(f)}{\hat{P}_r(f)}, \tag{11a}$$

where:
$\hat{H}_{br}(f)$ is the arterial pressure transfer function of the input signal between the brachial artery measurement location and the radial artery measurement location
$\hat{P}_b(f)$ is the Fourier transform of the brachial time-varying blood pressure pulse wave $P_b(t)$ at the brachial artery measurement location; and
$\hat{P}_{P_r}(f)$ is the Fourier transform of the radial time-varying blood pressure pulse wave $P_r(t)$ at the radial artery measurement location.

Figure 5:
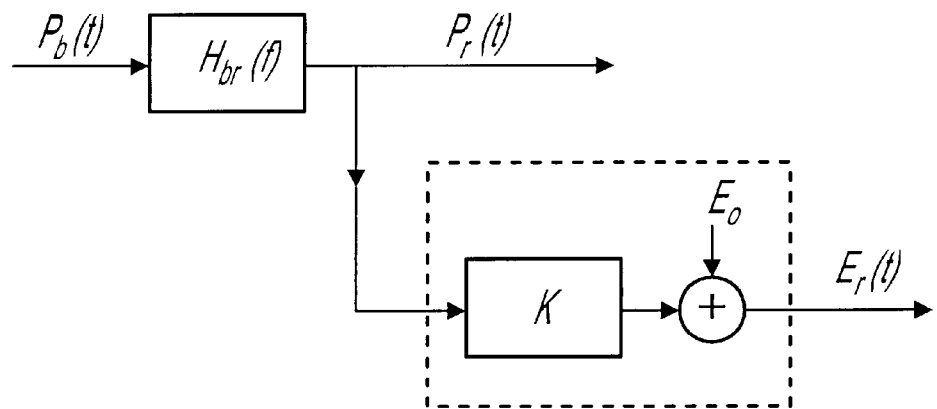
FIG. 5 is a schematic diagram of one exemplary embodiment of a physical system that converts a known physical phenomenon to an unknown physical phenomenon and an uncalibrated measurement device usable to measure the unknown physical phenomenon.

FIG. 5 shows a schematic diagram of one exemplary embodiment of a physical system that converts a known physical phenomenon to an unknown physical phenomenon and an uncalibrated device that can be used to measure the unknown physical phenomenon. In particular, in FIG. 5, a blood pressure pulse wave is used as the physical phenomenon. The known physical phenomenon is the brachial blood pressure pulse wave $P_b(t)$ that can be measured by a calibrated measurement device, such as an occlusion cuff. The brachial artery-to-radial artery transfer function $\hat{H}_{br}(f)$, as shown in Eq. (11a), converts the known brachial blood pressure pulse wave $P_b(t)$ to the unknown radial blood pressure pulse wave $P_r(t)$. The uncalibrated measurement device converts the unknown radial blood pressure pulse wave $P_r(t)$ to a uncalibrated measurement signal $E_r(t)$ based on an unknown proportionally constant K and an unknown calibration offset $E_o$, as defined using Eq. (1).

It should be appreciated that determining the calibration coefficient $C_c$ and the calibration constant $I_0$ of Eq. (2) is impossible until at least one frequency value for the transfer function $\hat{H}_{ab}(f)$ between the first and second measurement locations, such as the brachial-radial blood pressure transfer function $\hat{H}_{br}(f)$, is known.

Figure 6:
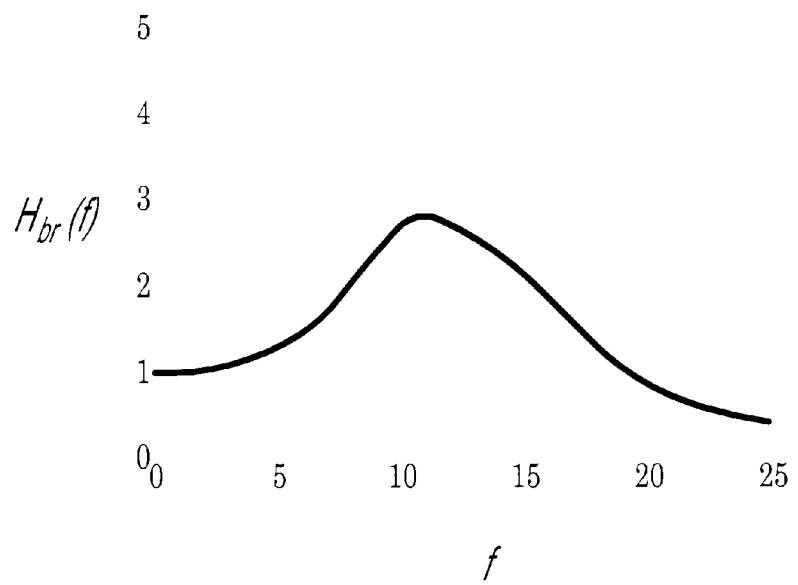
FIG. 6 is a graph plotting the magnitude of the brachial-to-radial transfer function as a function of frequency.

FIG. 6 shows an experimentally-determined frequency response of the brachial-radial blood pressure transfer function $\hat{H}_{br}(f)$ between the brachial artery blood pressure pulse wave and the radial artery blood pressure pulse wave. As shown in FIG. 6, the brachial-radial blood pressure transfer function $\hat{H}_{br}(f)$ reveals that the propagation characteristics of the blood pressure pulse wave are those of a resonant system. In a resonant system, the frequency components of the blood pressure pulse wave near the resonance frequency, that is, near the peak of the brachial-radial blood pressure transfer function $\hat{H}_{br}(f)$, are amplified relative to those frequency components at other frequencies. The brachial-radial blood pressure transfer function $\hat{H}_{br}(f)$ shown in FIG. 6 illustrates the distortion of various frequency components of the blood pressure pulse wave measured at the radial artery measurement location relative to the frequency components of the blood pressure pulse wave measured at the brachial artery measurement location.

Additionally, the brachial-radial blood pressure transfer function $H_{br}(f)$ shown in FIG. 6 depicts a useful characteristic of the system. This useful characteristic is that the brachial-radial blood pressure transfer function $\hat{H}_{br}(f)$ approaches a value of one as the frequency approaches zero, which may be described by the equations:

$$\hat{H}_{br}(0) = \frac{\hat{P}_r(0)}{\hat{P}_b(0)} = \frac{\overline{P}_r}{\overline{P}_b} = 1 \text{ or } \overline{P}_b \approx \overline{P}_r. \tag{12}$$

where:

$\hat{H}_{br}(0)$ is the value of the brachial-radial blood pressure transfer function $H_a(f)$ for a frequency of zero;

$\hat{P}_b(0)$ is the value of the Fourier transform of the time-varying brachial artery blood pressure pulse wave signal $P_b(t)$ for a frequency of zero;

$\overline{P}_b$ is the mean value of $P_b(t)$;

$\hat{P}_r(0)$ is the value of the Fourier transform of the time-varying radial brachial artery blood pressure pulse wave signal $P_r(t)$ for a frequency of zero; and $\overline{P}_r$ is the mean value of $P_r(t)$.

In essence, Eqs. (11a) and (12) mean that the average blood pressures or DC components of the radial and brachial arterial blood pressure pulse waves are equal. This statement is valid for the large arteries of the body, such as the brachial and radial arteries, used in an exemplary embodiment of the systems and methods according to this invention. Although the brachial-radial blood pressure transfer function $\hat{H}_{br}(f)$ is generally unknown, Eq. (12) provides, for many cases, the amplitude values of frequency components of a blood pressure signal approaching zero frequency when a blood pressure pulse is transmitted a distance through the vascular system. This information is used by various exemplary embodiments of the systems and methods according to this invention to calibrate an uncalibrated blood pressure measuring device.

More generally, if the general transfer function $\hat{H}_{ab}(f)$ has one or more frequency components ($f_1, f_2, \ldots$) having a known or determinable relationship, such as that shown in FIG. 6 for the zero-frequency components of the system shown in FIG. 5 for the brachial-radial blood pressure pulse wave transfer function $\hat{H}_{br}(f)$, then Eq. (12) can be used for those one or more frequency components ($f_1, f_2, \ldots$) to determine the amplitude values for those one or more frequency components ($f_1, f_2, \ldots$) of the transfer function $\hat{H}_{ab}(f)$.

An input signal-to-output signal transfer function, $\hat{H}_{IO}(f)=K\hat{H}_{ab}(f)$, can be defined for the input signal measured by a calibrated measuring device located at the first measurement location "a" and an output signal generated by an uncalibrated transducer located at the second measurement location "b".

For the one or more frequency components, such as an "$f_1$" frequency component, of the input and output signals for which the transfer function $\hat{H}_{ab}(f)$ has a known or determinable value, the value of the input signal-to-output signal transfer function $\hat{H}_{IO}(f_1)$ is:

$$\hat{H}_{IO}(f_1)=K\hat{H}_{ab}(f_1). \tag{13}$$

where:

$\hat{H}_{IO}(f_1)$ is the value of the transfer function $\hat{H}_{IO}(f)$ for the frequency $f_1$;

K is the constant of proportionality (from Eq. (1)); and $\hat{H}_{ab}(f_1)$ is the value of the transfer function $\hat{H}_{ab}(f)$ for the frequency of $f_1$.

For the system shown in FIG. 5, the input signal-to-output signal transfer function $\hat{H}_{IO}(f)$ is a pressure-to-voltage signal transfer function $\hat{H}_{pv}(f)$. As indicated above, the first location-to-second location transfer function $\hat{H}_{ab}(f)$ for this system is the brachial-radial blood pressure transfer function $\hat{H}_{br}(f)$. As illustrated in FIG. 6 and indicated by Eq. (12), $\overline{P}_r = \overline{P}_b$. Thus, Eq. (13) can be rewritten for the DC components of the brachial artery blood pressure pulse wave and the generated electrical signal as:

$$\hat{H}_{pv}(0)=K\hat{H}_{br}(0)=K \tag{13a}$$

where:

$\hat{H}_{pv}(0)$ is the value of the pressure-to-voltage transfer function $\hat{H}_{pv}(f)$ for a frequency of zero;

K is the constant of proportionality (from Eq. (1)); and $\hat{H}_{br}(0)$ is the value of the brachial-radial blood pressure transfer function $\hat{H}_{br}(f)$ for a frequency of zero.

If the technique used for estimating the input signal-to-output signal transfer function $\hat{H}_{IO}(f)$ does not estimate a phase angle, then the sign of K must be assigned from knowledge of the data. The value of K will be positive in most cases because the measured output signal $O_2(t)$ will be in phase with the calibrated input signal $I_1(t)$. Thus, when $O_2(t)$ and $I_1(t)$ are in phase:

$$K = \frac{|\hat{H}_{IO}(f_1)|}{|\hat{H}_{AB}(f_1)|}. \tag{14}$$

When $O_2(t)$ is inverted relative to the calibrated input signal $I_1(t)$, K is negative. That is:

$$K = \frac{|\hat{H}_{IO}(f_1)|}{|\hat{H}_{AB}(f_1)|}. \tag{15}$$

Figure 7:
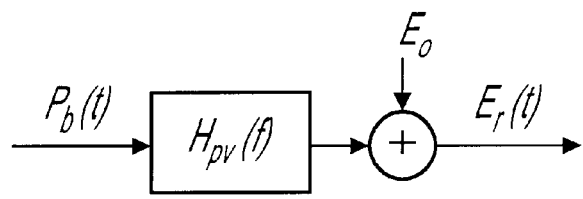
FIG. 7 is a schematic diagram of one exemplary embodiment of the uncalibrated measurement device based on an input signal/output signal transfer function between the input signals measured by the calibrated device and the output signals generated by the uncalibrated device.
Figure 8:
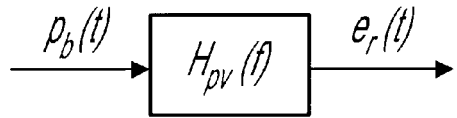
FIG. 8 illustrates FIG. 7 redrawn for non-zero-frequency signal components.

Since $O_2(t)$ depends on a time-varying component, $o_2(t)$, and an unknown zero frequency component, $O_0$, determining $\hat{H}_{IO}(f_1)$ for the frequency f, that has known or determinable values is impossible from the signals $O_2(t)$ and $1_1(t)$. However, if $\hat{H}_{IO}(f)$ is a well-behaved function of frequency, it is possible to take advantage of that fact. The input signal-to-output signal transfer function $\hat{H}_{IO}(f)$ can be experimentally determined for frequencies approaching the one or more of the frequency components ($f_1, f_2, \ldots$) that have known or determinable values. For example, for the pressure-to-voltage transfer function $\hat{H}_{pv}(f)$, the values for this transfer function $\hat{H}_{pv}(f)$ can be experimentally determined for frequencies approaching zero. For the input signal-to-output signal transfer function $\hat{H}_{IO}(f)$, the $f_1$ frequency value of the input signal-to-output signal transfer function $\hat{H}_{IO}(f_1)$ can be estimated from determining the frequencies approaching $f_1$. For example, for the pressureto-voltage transfer function $\hat{H}_{pv}(f)$, the zero frequency value can be estimated from this determination. For the pressure-to-voltage transfer function $\hat{H}_{pv}(f)$, or for any other transfer function that uses the zero-frequency component, the addition of $O_0$ has no effect on the AC components of the signal. Therefore, FIG. 8 shows FIG. 7 redrawn for AC-only analysis.

Determining the input signal-to-output signal $\hat{H}_{IO}(f)$ from $O_2(t)$ and $I_1(t)$ is a system identification problem that may be addressed by various techniques. Once K is determined from the absolute value of the estimate of the input signal-to-output signal $\hat{H}_{IO}(f)$ at $f \approx f_1$, the calibration coefficient $C_c$ is equal to the reciprocal of K, as given in Eq. (3).

Having obtained the calibration coefficient $C_c$, the calibration constant of the offset input signal value $I_0$ can be obtained by using estimates of the average values of the measured input signals, as described below. For transfer functions, such as the transfer function $\hat{H}_{pv}(f)$, for which Eq. (12) holds, Eq. (12) may be rewritten and extended as:

$$\bar{I}_1 = \bar{I}_2. \tag{16}$$

Similarly, Eq. 2 can be rewritten in view of 12 and $O_2$ as:

$$\bar{I}_2 = C_c \bar{O}_2 + I_0. \tag{17}$$

Combining Eqs. (16) and (17) and solving for $I_0$ yields:

$$I_0 = \bar{I}_1 - C_c \bar{O}_2. \tag{18}$$

Thus, for transfer functions, such as the transfer function $\hat{H}_{pv}(f)$ for which Eq. (12) holds, the calibration constant of the offset input signal value $I_0$ can be determined from the derived calibration coefficient $C_c$ and the average values of the input signals $\bar{I}_1$, and $\bar{I}_2$ used to determine the calibration coefficient $C_c$.

Figure 9:
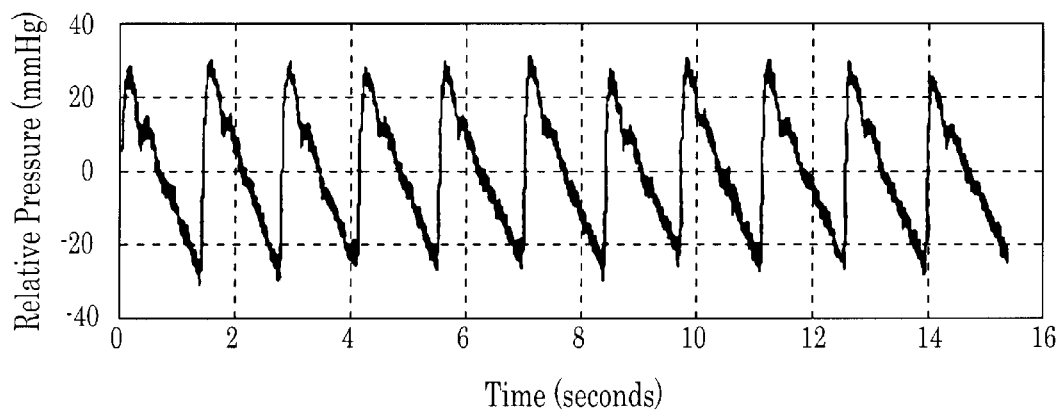
FIG. 9 is a graph plotting a calibrated input signal measured at a first location of the system being measured, where the zero-frequency component has been removed.
Figure 10:
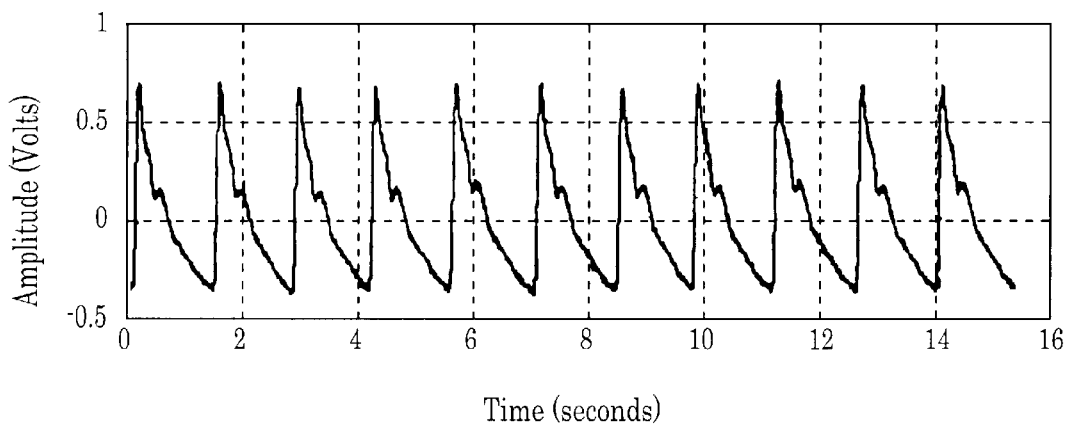
FIG. 10 is a graph plotting the output signal of an uncalibrated measurement device measured at a second location of the system being measured, where the zero-frequency component has been removed.

In general, determining the calibration coefficient $C_c$ based on Eqs. (13)–(17) is most easily used with experimental data that characterizes the input signal-to-output signal transfer function $\hat{H}_{IO}(f)$ for frequencies approaching zero. There are techniques for characterizing transfer functions from a sample of input and output data. Generally, such techniques are either parametric or non-parametric transfer function estimations. FIG. 9 is a graph plotting experimental data of the time-varying components of the calibrated brachial artery blood pressure signal, $p_1(t)$. In the graph shown in FIG. 9, the average DC component $\bar{P}_1$, which is equal to 70 mm of Hg, has been removed. FIG. 10 is a graph plotting the time-varying components of the uncalibrated radial artery blood pressure signal $e_2(t)$. Again, in the graph shown in FIG. 10, the average DC component $\bar{E}_2$, which is equal to 0.33 mV, has been removed. The signals shown in FIGS. 9 and 10 are digitized samples of the continuous signals with a sampling rate of 250 samples/sec.

Non-parametric techniques are generally based on transforming the input and output time functions into the frequency domain. The most common transformation for digitized data is the Discrete Fourier Transform (DFT). When the duration of the signal is equal to a power of 2, the Discrete Fourier Transform can be implemented efficiently using a Fast Fourier Transform (FFT) algorithm. The most commonly used Discrete Fourier Transform-based method for determining the estimated input signal-to-output signal transfer function $\hat{H}_{IO}(f)$ is:

$$\hat{H}_{IO}(f) = \frac{DFT\{E[o_2(t)o_2(t+\tau)]W(\tau)\}}{DFT\{E[o_2(t)i_1(t+\tau)]W(\tau)\}}, \tag{19}$$

where:

E[ . . . ] is the statistical expectation operator; and $W(\tau)$ is a windowing function, for example, a Hamming window.

In this exemplary embodiment, the function $E[o_2(t)o_2(t+\tau)]$ is the auto-correlation function of $O_2(t)$ and the function $E[o_2(t+\tau)]$ is the cross-correlation of $o_2(t)$ with $i_1(t)$. In Eq. (19), the effect of multiplying the auto-correlation and cross-correlation functions by the window function $W(\tau)$ is to smooth the frequency estimates, where the amount of frequency smoothing is inversely proportional to the width of the window function.

Figure 11:
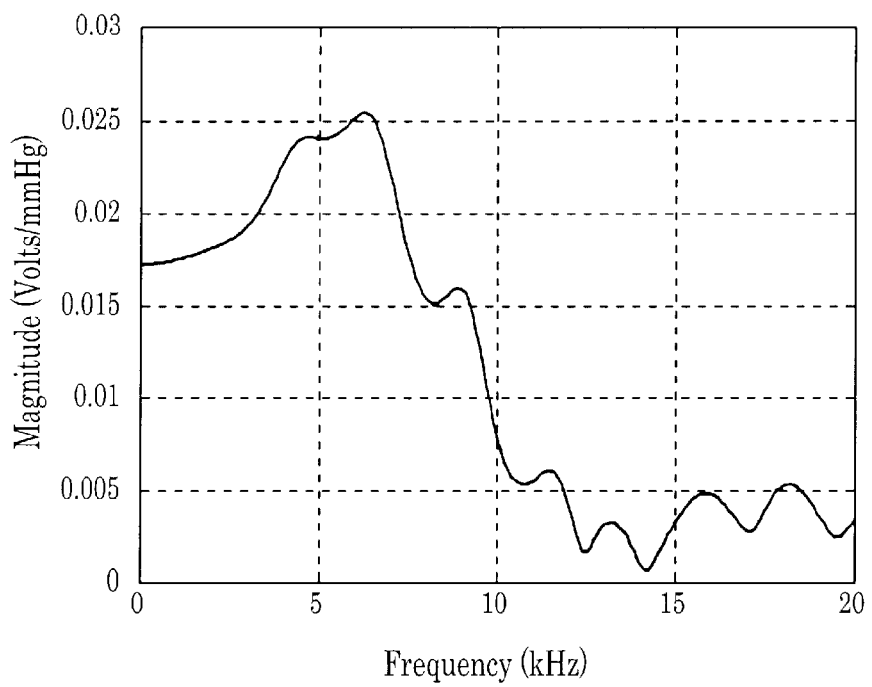
FIG. 11 is a graph plotting the input signal/output signal transfer function, shown in FIGS. 7 and 8, based on the graphs shown in FIGS. 9 and 10.
Figure 12:
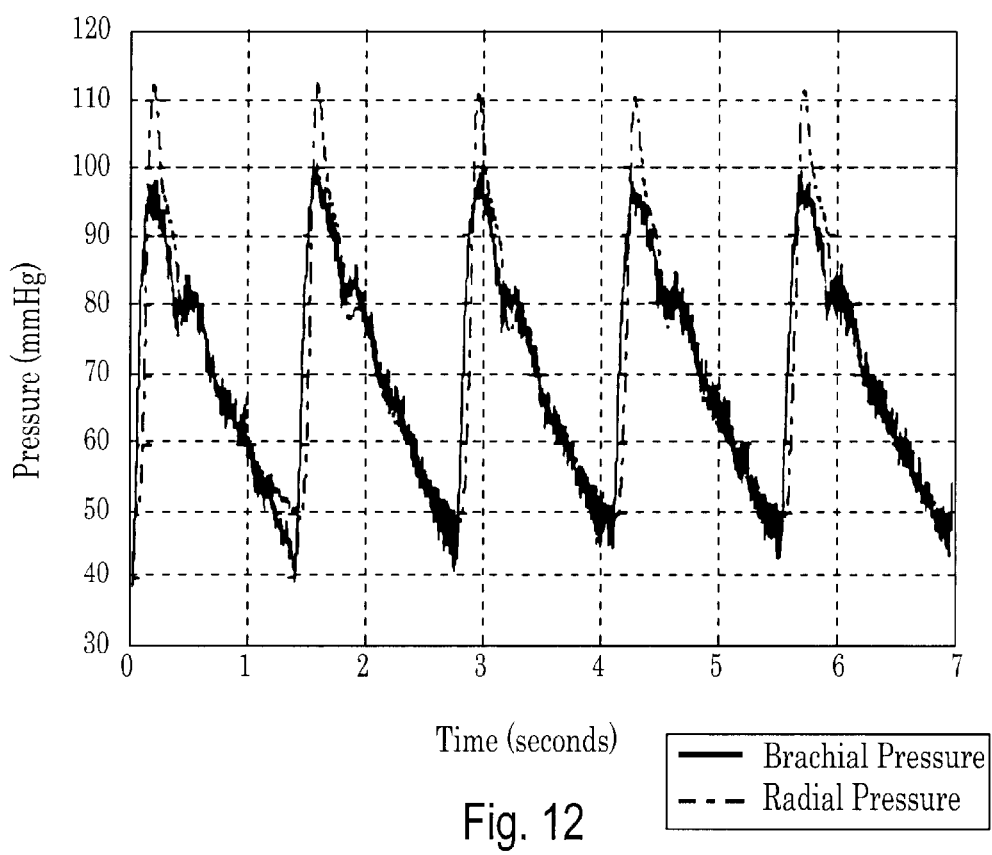
FIG. 12 is a graph plotting the value of the input signal measured at a first location of the system using the calibrated device and the value of the input signal measured by the device at a second location, after calibration according to the systems and methods of this invention.

FIG. 11 shows the absolute value of the estimated pressure-to-voltage transfer function $\hat{H}_{pv}(f)$ obtained using the data shown in FIGS. 9 and 10. Using the estimated pressure-to-voltage transfer function $\hat{H}pv(f)$ provided by the data shown in FIG. 11, K is 0.0172 volts/mm of Hg and is derived based on Eq. (13a). Once K is determined, based on Eq. (3), the calibration coefficient $C_c$ is 58.1 mm of Hg/volt. Once the calibration coefficient $C_c$ is determined, based on Eq. (4) or Eq. (18), the calibration constant $I_0$ is 69.98 mm of Hg. FIG. 12 is a graph plotting the calibrated brachial blood pressure pulse wave $P_1(t)$ and the radial blood pressure pulse wave $P_2(t)$ calibrated using the calibration coefficient $C_c$, where $C_c$=58.1 mm of Hg/volt, as determined above.

One parametric technique for determining a transfer function H(f) is the auto-regression (AR) technique. In the auto-regression technique, a transfer function H(z) in the form of a fraction of polynomials in the complex z-domain is determined. The z-domain transfer function H(z) will have a polynomial numerator of order $N_b-1$ and a polynomial denominator of order $N_a$ and will be in the form:

$$\hat{H}_{IO}(z) = \frac{\sum_{n=1}^{N_b} b_n z^{-(n-1)}}{1 + \sum_{n=1}^{N_a} a_n z^{-n}}. \tag{20}$$

The coefficients $a_n$ and $b_n$ are determined so that the estimated input signal-to-output signal transfer function $\hat{H}_{IO}(z)$ is the optimal polynomial transfer function, according to a least-squares method.

A property of the z-transform is that the Fourier transform can be found from the z-transform by simply substituting:

$$z = e^{j2\pi f}. \tag{21}$$

Figure 13:
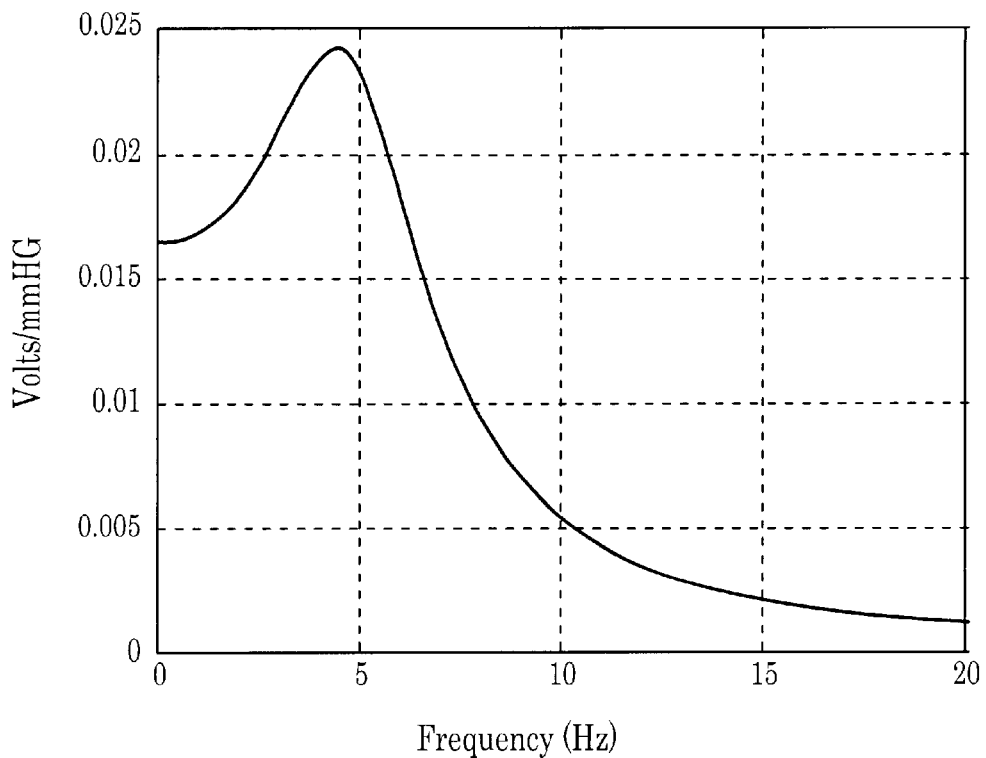
FIG. 13 is a graph plotting the estimated input signal/output signal transfer function obtained using a low-order ARX model.

Using this substitution, FIG. 13 shows the absolute value of the estimated pressure-to-voltage transfer function $|\hat{H}_{pv}(f)|$, determined using the data shown in FIGS. 9 and 10, with the auto-regression model described in Eq. (20), where $N_a=2$ and $N_b=1$. Eq. (21) and Eq. (14), rewritten for $\hat{H}_{pv}(f)$, may be combined to give:

$$K = \hat{H}_{pv}(f=0) = \hat{H}_{pv}(z=1) = \frac{\sum_{n=1}^{N_b} b_n}{1 + \sum_{n=1}^{N_a} a_n}. \quad (22)$$

Using the estimated input signal-to-output signal transfer function $\hat{H}_{IO}(z)$ determined by the auto-regression technique, as shown in FIG. 13, when Eq. (22) is used, with $N_a=2$ and $N_b=1$, K is equal to 0.0164 volts/mm of Hg.

In various exemplary embodiments of the systems and methods according to this invention, the uncalibrated sensor or transducer may be calibrated using either parametric or non-parametric techniques to determine an estimated transfer function. The particular technique implemented will depend largely on the application and/or the measuring device being calibrated. The non-parametric technique is usually more computationally intensive, but it may be more generally applied to systems where the nature of the transfer function is not well known. In systems where the general nature of the transfer function is known and the transfer function may be modeled by a relatively low-order polynomial fraction, a parametric technique can be very computationally efficient. For example, when calibrating the electronic tonometer placed over the radial artery based on the data shown in FIGS. 9 and 10, the pressure-to-voltage transfer function $H_{pv}(f)$ at frequencies near zero is well approximated by a second-order function of polynomials, i.e., by setting $N_a=2$ and $N_b=1$.

An exemplary embodiment of the systems and methods according to this invention has been described relative to calibrating an electronic tonometer using an oscillometric blood pressure cuff monitor as the calibration standard. In various other exemplary embodiments, other volumetric or pressure transducers that are to be calibrated may be used to measure the blood pressure and calibrated devices other than the calibrated oscillometric blood pressure cuff may be used. The electronic tonometer may be placed, for example, on the wrist of an individual, where the tonometer will produce an electrical signal $E_2(t)$ proportional to a blood pressure signal $P_2(t)$ of the radial artery. The electrical signal $E_2(t)$ may be continuous or discrete. The blood pressure signal output by the electronic tonometer has an average constant component $\overline{E}_2$ that is a function of the electronic circuitry of the tonometer, the average measured arterial blood pressure, and the average transmural pressure of the artery being measured.

As described above, in various exemplary embodiments, the calibrated oscillometric blood pressure monitor is an air-filled occlusive cuff, which may determine the maximum (systolic), average, and minimum (diastolic) blood pressures of, for example, the brachial artery. These blood pressure measures are produced by time-varying changes in the transmural blood pressure of the artery. The time-varying changes in the transmural blood pressure in turn cause volumetric changes of the artery that are transmitted through the overlying tissues to the surface of the skin, where the air-filled occlusive cuff responds to volumetric changes by producing pressure fluctuations in the air-filled occlusive cuff. The amplitude of the pressure fluctuations in the air-filled occlusive cuff and thus, the pressure signals of the oscillometric blood pressure monitor, are a function of the volume of the air-filled occlusive cuff, the differences between the cuff pressures and the arterial pressures (the transmural pressures), the elasticity of the arterial wall, the electrical characteristics of oscillometric blood pressure monitor, and the frequency responses of the air-filled occlusive cuff, the overlying tissues, the air-filled connector tubing. The oscillometric blood pressure monitor may measure the blood pressure continuously or discretely.

Figure 14:
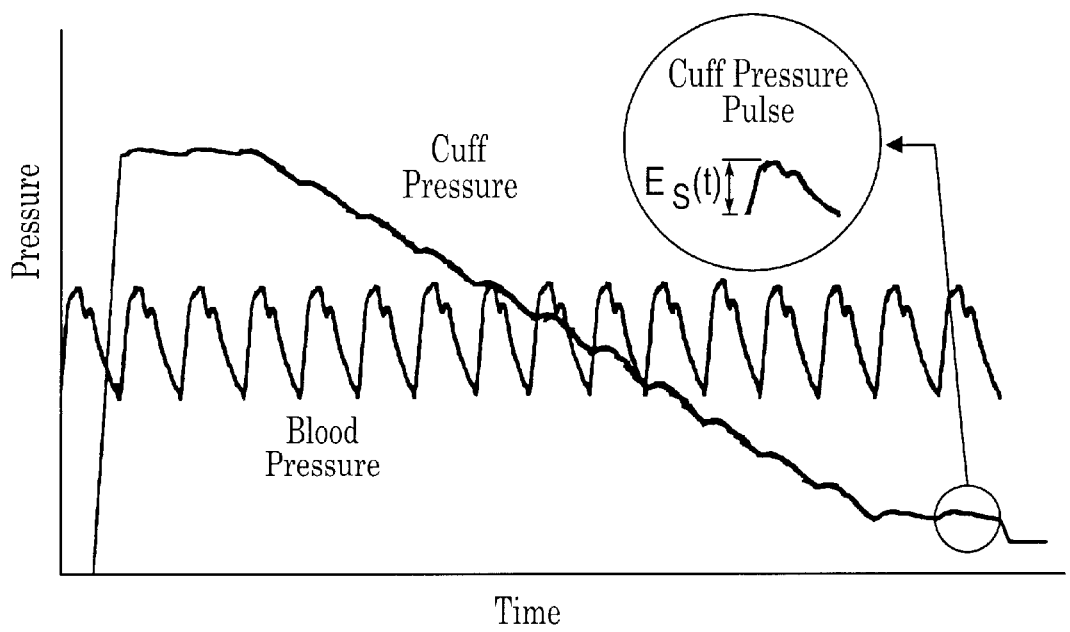
FIG. 14 is a graph plotting pressure versus time for pressure sensed by a blood pressure measurement device and for arterial blood pressure pulses.

When the transmural pressure differences are small, the shape of the blood pressure signals measured by the oscillometric blood pressure monitor will closely approximate those of the internal blood pressure signal of the artery. The technique of measuring the blood pressure signal when the transmural pressure differences are small is known as plethysmographic measurement. As shown in FIG. 14, plethysmographic measurements are made at the end of the oscillometric blood pressure measurement cycle. If the plethysmographic measurements are digitized, the measures may be used directly, after possible scaling, in determining the calibration coefficient and the calibration constant, using, for example, a general purpose computer, a personal computer, a microprocessor, a digital signal processor or any equivalent device or circuit. If the plethysmographic measurements are analog, the measures must first be digitized, for example, by an analog-to-digital converter, before the digitized measurements can be used. By measuring an electrical signal E(t) from an electronic tonometer, the blood pressure P(t) is:

$$P(t) = C_{pv}E(t) + P_o, \quad (23)$$

where:
(t) is the time-varying blood pressure of a living being;
$C_{pv}$ is the calibration coefficient for a blood pressure-to-voltage transducer;
E(t) is the time-varying electrical signal generated by sensing the time-varying blood pressure of the living being; and
$P_o$ is calibration constant for this blood pressure-to-voltage transducer.

The blood pressure-to-voltage calibration coefficient $C_{pv}$ and blood pressure calibration constant $P_o$ may be found by using the average, diastolic and systolic pressures measured by a non-invasive blood pressure (NIBP) monitor, as described above relative to an air-filled occlusion cuff.

For a plethysmographic measurement, if the average blood pressure is $\overline{P}$, the calibration coefficient $C_{pv}$ is:

$$C_{pv} = \frac{P_S - P_D}{E_S - E_D}, \quad (24)$$

where:
$P_S$ is the systolic blood pressure of the living being;
$P_D$ is the diastolic blood pressure of the living being;
$E_S$ is the value of the time-varying electrical signal that corresponds to the systolic blood pressure $P_S$ of the living being; and
$E_D$ is the value of the time-varying electrical signal that corresponds to the diastolic blood pressure $P_D$ of the living being.

Accordingly, based on rewriting Eq. (23), the calibration constant $P_o$ is:

$$P_o = \overline{P} - C_{pv}\overline{E}. \quad (25)$$

Figure 15:
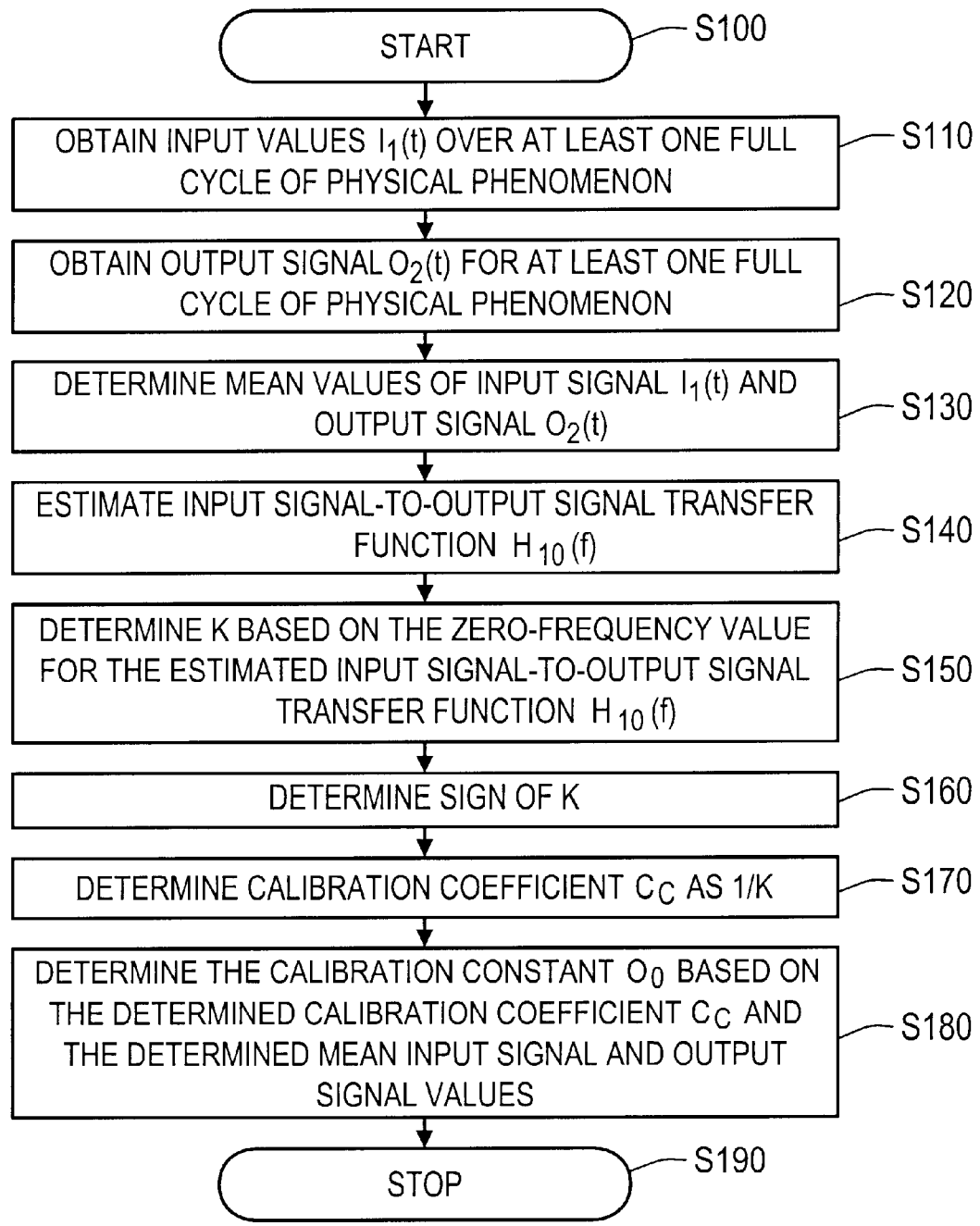
FIG. 15 is a flowchart outlining one exemplary embodiment of a method for calibrating an uncalibrated sensor or transducer according to this invention.

FIG. 15 is a flowchart outlining one exemplary embodiment of a method for calibrating an uncalibrated sensor or transducer according to this invention. In particular, in the flowchart shown in FIG. 15, the uncalibrated sensor is located at a second location B relative to the system being sensed that is spaced away from a first location A of a calibrated sensor that has been previously calibrated to the system being sensed.

As shown in FIG. 15, operation of the method begins in step S100, and continues to step S110, where input values $I_1(t)$ of the physical phenomenon are obtained from the calibrated sensor at the first location A over at least one full cycle of the periodic physical phenomenon of the system that is being sensed by the calibrated and uncalibrated sensors. Then, in step S120, the output signal $O_2(t)$ is obtained from the uncalibrated sensor at the second location B for at least one full cycle of the physical phenomenon of the system. In general, steps S110 and 120 will often occur simultaneously, so that the system being sensed is in the same state for both measurements. However, it should be appreciated that steps S110 and 120 do not necessarily need to be performed simultaneously so long as the system being sensed is in substantially the same state when each of steps S110 and 120 are performed. Operation then continues to step S130.

In step S130, the mean values of $\bar{I}$ and $\bar{O}$ of the input signal $I_1(t)$ and the output signal $O_2(t)$ are determined. Next, in step S140, the input signal-to-output signal transfer function $\hat{H}_{IO}(f)$ is estimated. It should be appreciated that the estimated input signal-to-output signal transfer function can be estimated using either parametric or non-parametric methods. In particular, any known or later-developed method for estimating the estimated input signal-to-output signal transfer function can be used. Then, in step S150, the value of K is determined based on the zero-frequency value for the estimated input signal-to-output signal transfer function $\hat{H}_{IO}(f)$. Operation then continues to step S160.

In step S160, the sign of K is determined. As indicated above, if the measured output signal $O_2(t)$ follows the input signal $I_1(t)$, the sign of K will be positive. In contrast, if the output signal $O_2(t)$ is inverted relative to the input signal $I_1(t)$, K will be negative. If the phase of the input signal-to-output signal transfer function $\hat{H}_{IO}(f)$ is known, the sign of K can be readily determined. If the phase of the transfer function is not known, the phase of the estimated input signal-to-output signal transfer function can be determined to determine the sign of K. Operation then continues to step S170.

In step S170, the calibration coefficient $C_c$ is determined as the reciprocal of K. Next, in step S 180, the calibration constant $O_0$ is determined based on the determined calibration coefficient $C_c$ and the determined mean input signal and output signal values $\bar{I}$ and $\bar{O}$. Then in step S 190, operation of the method ends.

Figure 16:
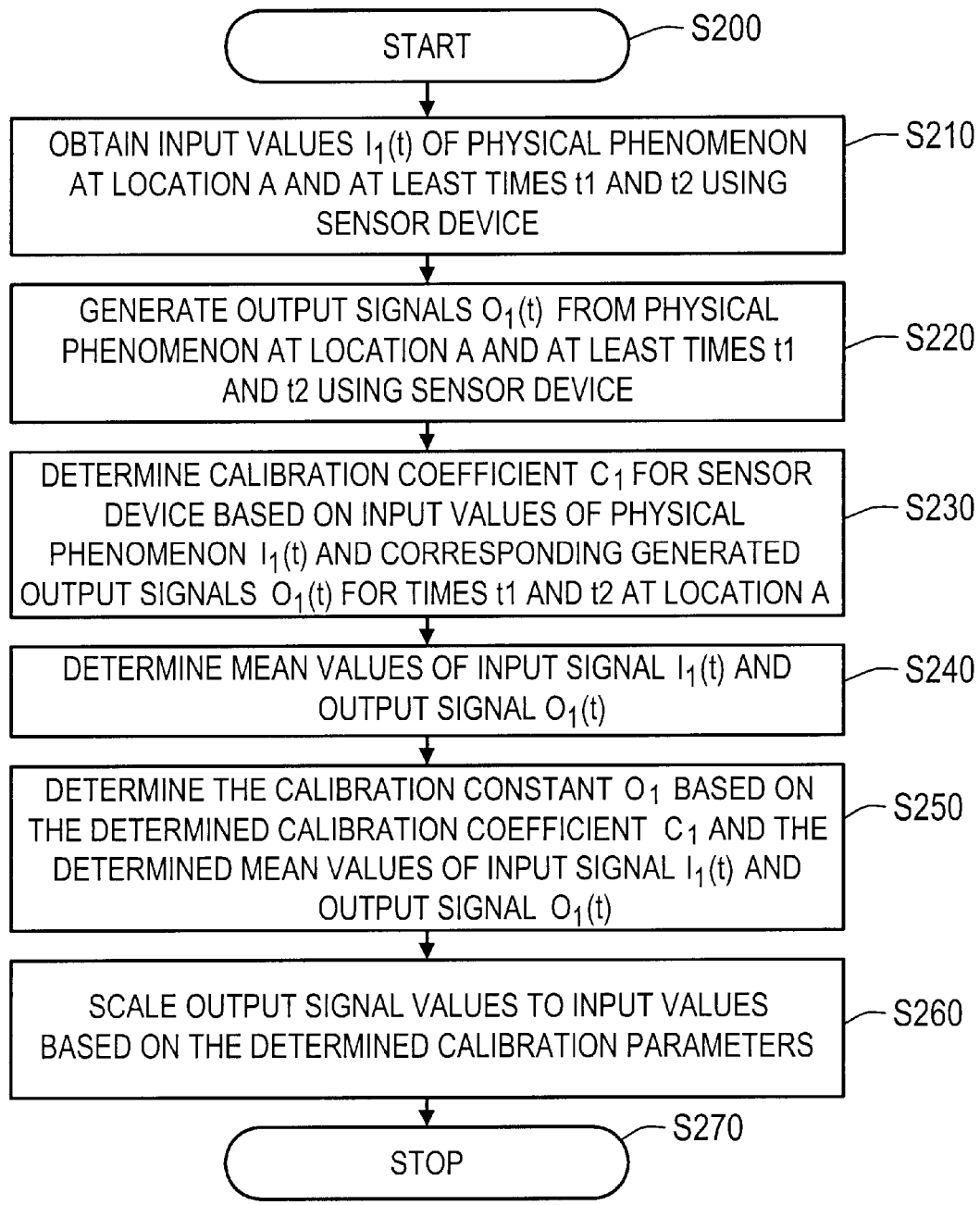
FIG. 16 is a flowchart outlining one exemplary embodiment of a method for ensuring the calibrated sensor device used in the flowchart of FIG. 15 is properly calibrated to the system.

FIG. 16 is a flowchart outlining one exemplary embodiment of a method for ensuring that the calibrated first sensor placed at the first location A relative to the system being sensed is properly calibrated to the system being sensed. As outlined above, the flowchart outlined with respect to FIG. 15 assumes that the calibrated sensor is properly calibrated to the system being sensed. The method outlined in FIG. 16 can be used to calibrate a sensor so that that sensor can be used as the calibrated sensor in the method outlined in FIG. 15.

As shown in FIG. 16, operation of the method begins in step S200 and continues to step S210, wherein input values $I_1(t)$ of the physical phenomenon being sensed at location A are obtained for at least first and second times $t_1$ and $t_2$ using the first sensor placed at the first location A relative to the system being sensed. Then, in step S220, output signals $O_1(t)$ from the first sensor are generated or obtained in response to the physical phenomenon being sensed in the system being sensed at the first location A and for at least the times $t_1$ and $t_2$ using the first sensor. Next, in step S230, the calibration coefficient $C_c$ for the first sensor is determined based on the input values $I_1(t_1)$ and $I_1(t_2)$ of the physical phenomenon being sensed and the corresponding generated output signals $O_1(t_1)$ and $O_1(t_2)$ from the sensor device located at the first location A relative to the system being sensed. Operation then continues to step S240.

In step S240, mean values $\hat{I}$ and $\hat{O}$ of the input signal $I_1(t)$ and the output signal $O_1(t)$, respectively, are determined based at least in part on the input values $I_1(t)$ and the output signals $O_1(t)$ determined in steps S210 and 220. Next, in step S250, the calibration constant $O_1$ is determined based on the determined calibration coefficient $C_1$ and the determined mean input signal and output signal values $\hat{I}$ and $\hat{O}$. Then, in step S260, the output signal values are scaled to the input values based on the determined calibration parameters. Operation then continues to step S270, where operation of the method ends.

Figure 17:
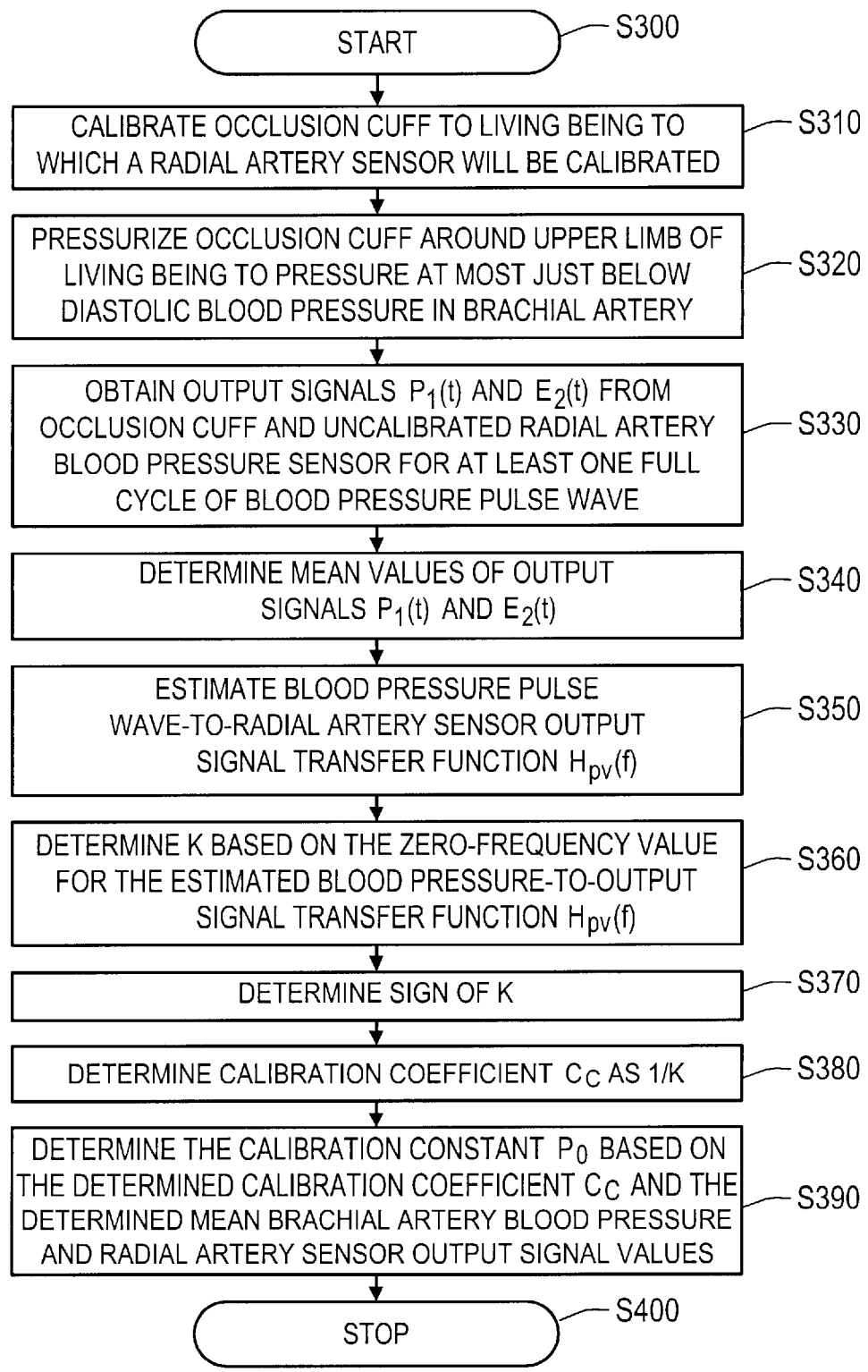
FIG. 17 is a flowchart outlining one exemplary embodiment of a method for calibrating a blood pressure occlusion cuff relative to the brachial artery pressure in a living being and for using the calibrated occlusion cuff to calibrate an uncalibrated radial artery blood pressure sensor according to this invention.

FIG. 17 is a flowchart outlining one exemplary embodiment of applying the methods outlined above in FIGS. 15 and 16 to calibrating a radial artery blood pressure sensor, such as a radial tonometer, using an occlusion cuff blood pressure sensor placed on a living being to sense the brachial artery blood pressure. In particular, as shown in FIG. 17, operation of the method begins in step S300 and continues to step S310, where the occlusion cuff is itself calibrated to the living being to which the radial tonometer will be calibrated using the systems and methods according to this invention. Operation then continues to step S320.

It should be appreciated that any known or later-developed method or technique for calibrating the occlusion cuff to the living being can be used in step S310. Additionally, it should be appreciated that step S310 can be omitted either if the occlusion cuff has already been calibrated to this living being, or if the occlusion cuff has been generally calibrated by determining generalized calibration parameters that are usable relative to this living being. For example, if most human beings have substantially similar calibration parameters for the occlusion cuff, generalized calibration parameters usable with any human being can be determined to calibrate the occlusion cuff and used in the systems and methods according to this invention to calibrate the uncalibrated radial tonometer.

In step S320, the occlusion cuff is pressurized, by inflating or deflating the occlusion cuff, around the upper limb of the living being to a pressure that is at most just below the diastolic blood pressure in the brachial artery of that living being. It should be appreciated that the pressure in the occlusion cuff need not be close to the diastolic pressure. Then, in step S330, signals $P_1(t)$ and $E_2(t)$ are obtained from the occlusion cuff and the uncalibrated radial artery blood pressure sensor, respectively, for at least one full cycle of the blood pressure pulse wave. Next, in step 340, the mean values $\bar{P}$ and $\bar{E}_2$ for the signals $P_1(t)$ and $E_2(t)$, respectively, are determined. Operation then continues to step S350.

In step S350, the blood pressure pulse wave-to-radial artery sensor output signal transfer function $\hat{H}_{pv}(f)$ is estimated using any known or later developed parametric or non-parametric technique usable to estimate a transfer function in the frequency domain. Next, in step S360, the value of K is determined based on the zero-frequency value of the estimated blood pressure pulse wave-to-radial artery sensor output signal transfer function $\hat{H}_{pv}(0)$. Then, in step S370, the sign of K is determined as outlined above with respect to step S160. Operation then continues to step S380.

In step S380, the calibration coefficient $C_c$ for the uncalibrated radial artery sensor is determined as the reciprocal of K. Then, in step S390, the calibration constant $P_0$ for the uncalibrated radial artery sensor is determined based on the determined calibration coefficient $C_c$ and the determined mean brachial artery blood pressure $\overline{P}_1$ and the mean radial artery sensor output signal value $\overline{E}_2$. Operation then continues to step S400, where the operation of the method ends.

Figure 18:
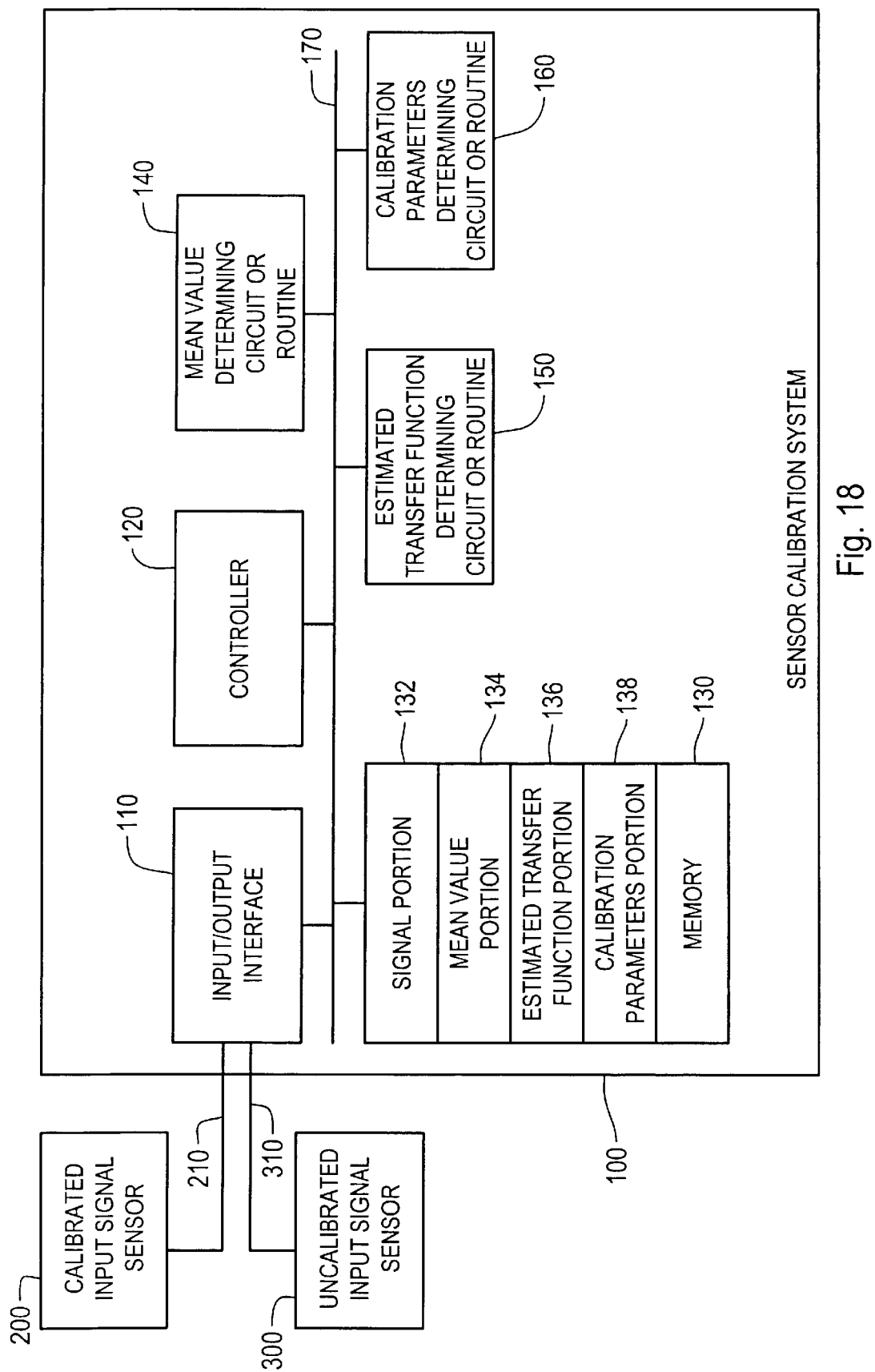
FIG. 18 is a block diagram of one exemplary system usable to calibrate an uncalibrated sensor or transducer according to this invention.

FIG. 18 is a block diagram outlining one exemplary embodiment of a sensor calibration system according to this invention. As shown in FIG. 18, the sensor calibration system 100 is connected to a calibrated input signal sensor 200 by a link 210 and to an uncalibrated input signal sensor 300 by a link 310. Each of the calibrated and uncalibrated input signal sensors 200 and 300 are attached to a system having a physical phenomenon to be sensed. In particular, the calibrated input signal sensor 200 is connected to the system at a first location A, while the uncalibrated input signal sensor 300 is attached to the system at a second location B that is spaced apart from the first location A.

The sensor calibration system 100 includes an input output interface 110 that inputs the signals over the links 210 and 310, a controller 120, a memory 130, a mean value determining circuit or routine 140, an estimated transfer function determining circuit or routine 150, and a calibration parameters determining circuit or routine 160, each interconnected by a control and/or data bus 170. The memory 130 includes a signal portion 132, a mean value portion 134, an estimated transfer function portion 136 and a calibration parameters portion 138.

The signal portion 132 stores the one or more full cycles of the periodic physical phenomenon being sensed output by each of the calibrated and uncalibrated input signal sensors 200 and 300. The mean value portion 134 stores the mean values determined by the mean value determining circuit or routine from the signals received from the calibrated and/or uncalibrated input signal sensors 200 and/or 300. The estimated transfer function portion 136 stores the estimated transfer function generated by the estimated transfer function determining circuit or routine 150. The calibration parameters portion 138 stores the calibration coefficient and the calibration constant determined by the calibration and parameters determining circuit or routine for the uncalibrated input signal sensor 300. The calibration parameters portion 138 can also store the calibration parameters determined by the sensor calibration system for the calibrated input signal sensor 200. Alternatively, the calibration parameters portion 138 can store predetermined calibration parameters for the calibrated input signal sensor 200.

In operation, under control of the controller 120 of the sensor calibration system 100, one or more of the calibrated input signal sensor 200 and the uncalibrated input signal sensor 300 generate output signals from the sensed physical phenomenon of the system being sensed. These output signals are provided by the one or more of the calibrated and/or uncalibrated input signal sensors 200 and/or 300 over the links 210 and/or 310, respectively, to the input output interface 110. The input output interface 110, under control of the controller 120, stores the signals in the signal portion 132 of the memory 130. Then, under control of the controller 120, the signals stored in the signal portion 132 are output to the mean value determining circuit or routine 140. The mean value determining circuit or routine 140 determines the mean values for the signals from each of the calibrated and uncalibrated input signal sensors 200 and 300. Then, under control of the controller 120, the mean values determined by the mean value determining circuit or routine are stored in the mean value portion 134.

Also under control of the controller 120, the signals stored in the signal portion 132 are provided to the estimated transfer function determining circuit or routine, which determines an estimated transfer function $\hat{H}_{IO}(f)$ from the input signal portions using any known or later developed parametric or non-parametric transfer function estimating technique or algorithm. Then, under control of the controller 120, the estimated transfer function is stored into the estimated transfer function portion 136. It should be appreciated that the estimated transfer function and determining circuit 150 can operate independently or concurrently with the mean value determining circuit 140.

Next, under control of the controller 120, the calibration parameters determining circuit or routine 160 inputs the estimated transfer function stored in the estimated transfer function portion and extracts a desired frequency component, such as, for example, the zero frequency component, of the estimated transfer function as the value of K. Next, the calibration parameters determining circuit or routine 160 determines the value of the calibration coefficient $C_c$ as the reciprocal of the value K. Then, the calibration parameters determining circuit or routine 160 determines the calibration constant $O_0$ based on the determined calibration coefficient $C_c$, the mean value of the output signal output by the uncalibrated input signal sensor 300, and the mean value of the physical phenomenon, which is obtained from the output signal output by the calibrated input signal sensor 200. The calibration parameters for the uncalibrated sensor 300 determined by the calibration parameters determining circuit or routine 160 are stored in the calibration parameters portion 138.

It should also be appreciated that, if the calibrated input signal sensor 200 needs to be calibrated for the particular location A of the system at which it is located, or for any other reason, the calibration parameters determining circuit or routine 160 can perform this operation. In particular, under control of the controller 120, the calibrated input signal sensor 200 is operated to generate signal values usable to calibrate the calibrated input signal sensor, such as those outlined above with respect to FIGS. 17A and 17B. These signal portions are input through the input/output interface 110 and, under control of the controller 120, are stored in the signal portion 132. Then, the calibration parameters determining circuit or routine 160 generates the calibration coefficient $C_{C1}$, for the calibrated input signal sensor 200 and the calibration constant $I_1$ for the calibrated input signal sensor 200.

The sensor calibration system 100 shown in FIG. 18 is, in various exemplary embodiments, implemented on a programmed general purpose computer. However, the sensor calibration system 100 can also be implemented on a special purpose computer, a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA or PAL, or the like. In general, any device, capable of implementing a finite state machine that is in turn capable of implementing the flowcharts shown in FIGS. 15–17B, can be used to implement the sensor calibration system 100.

It should be understood that each of the circuits shown in FIG. 18 can be implemented as portions of a suitably programmed general purpose computer. Alternatively, each of the circuits shown in FIG. 18 can be implemented as physically distinct hardware circuits within an ASIC, or using a FPGA, a PDL, a PLA or a PAL, or using discrete logic elements or discrete circuit elements. The particular form each of the circuits shown in FIG. 18 will take is a design choice and will be obvious and predicable to those skilled in the art.

Moreover, the sensor calibration system 100 can be implemented as software executing on a programmed general purpose computer, a special purpose computer, a microprocessor or the like. In this case, the sensor calibration system 100 can be implemented as a routine embedded in a sensor system, as a resource residing on a server, or the like. The sensor calibration system 100 can also be implemented by physically incorporating it into a software and/or hardware system.

The memory 130 shown in FIG. 18 can be implemented using any appropriate combination of alterable, volatile or non-volatile memory or non-alterable, or fixed, memory. The alterable memory, whether volatile or non-volatile, can be implemented using any one or more of static or dynamic RAM, a floppy disk and disk drive, a writable or re-writable optical disk and disk drive, a hard drive, flash memory or the like. Similarly, the non-alterable or fixed memory can be implemented using any one or more of ROM, PROM, EPROM, EEPROM, an optical ROM disk, such as a CD-ROM or DVD-ROM disk, and disk drive or the like.

The links 210 and 310 can each be any known or later developed device or system for connecting the sensors 200 and 300, respectively, to the sensor calibration system 100, including a connection through a public switched telephone network, a direct cable connection, a connection over a wide area network or a local area network, a connection over an intranet, a connection over the Internet, or a connection over any other distributed processing network or system. Further, it should be appreciated that, for each of the links 210 and 310 connecting the sensors 200 and 300, respectively, to the sensor calibration system 100, at least a portion of each such link can be a wired or wireless link In general, the links 210 and 310 can each any known or later developed connection system or structure usable to connect the scanner 100 to the scanned image registration system 200.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention as defined in the following claims.

What is claimed is:

1. A method for calibrating an uncalibrated sensor, comprising:

sensing at a first location a time-varying physical phenomenon using a calibrated sensor to determine an input waveform of the time-varying physical phenomenon at the first location;

sensing at a second location the time-varying physical phenomenon using the uncalibrated sensor, the uncalibrated sensor outputting an output waveform corresponding to the time-varying physical phenomenon at the second location;

determining a frequency-domain transfer function that relates the output waveform to the input waveform based on the input and output waveforms;

determining a calibration coefficient for the uncalibrated sensor based on the determined frequency-domain transfer function; and determining a calibration constant for the uncalibrated sensor based on the determined calibration coefficient, the input waveform and the output waveform, wherein the determined calibration coefficient and the determined calibration constant calibrate the uncalibrated sensor to the time-varying physical phenomenon at the second location.

2. The method of claim 1, wherein the time-varying physical phenomenon is blood pressure.

3. The method of claim 2, wherein the calibrated sensor is a calibrated oscillometric blood pressure monitor.

4. The method of claim 2, wherein the uncalibrated sensor is a tonometer.

5. The method of claim 4, wherein the tonometer is an electronic applanation tonometer.

6. The method of claim 1, wherein the calibrated sensor has a known frequency and amplitude response to the time-varying physical phenomenon at the first location.

7. The method of claim 1, wherein determining the frequency-domain transfer function based on the input and output waveforms comprises determining an estimated frequency-domain transfer function based on the input and output waveforms.

8. The method of claim 7, wherein determining the calibration coefficient for the uncalibrated sensor based on the determined frequency-domain transfer function comprises:

determining a value of the estimated frequency-domain transfer function at a frequency where a second frequency-domain transfer function that relates the input waveform to a second input waveform of the time-varying physical phenomenon at the second location has a determinable value;

determining the calibration coefficient based on the value of the estimated frequency-domain transfer function at the frequency and the determinable value of the second frequency-domain transfer function.

9. The method of claim 7, wherein the frequency is zero.

10. The method of claim 9, wherein the second frequency-domain transfer function has a value of 1 for the frequency of zero.

11. The method of claim 1, further comprising:

determining a mean value of the input waveform; and determining a mean value of the output waveform;

wherein determining the calibration constant for the uncalibrated sensor comprises determining the calibration constant based on the calibration coefficient, the mean value of the input waveform and the mean value of the output waveform.

12. The method of claim 1, wherein determining the frequency-domain transfer function that relates the output waveform to the input waveform based on the input and output waveforms comprises:

obtaining at least one full waveform for each of the input and output waveforms;

defining an estimated transfer function in the complex z-domain that corresponds to the frequency-domain transfer function, the estimated z-domain transfer function having a plurality of parameters; and determining values for the parameters such that the estimated z-domain transfer function is fitted to the obtained at least one full waveforms for the input and output waveforms.

converting the fitted z-domain transfer function to the frequency-domain transfer function.

13. The method of claim 12, further comprising:

determining a frequency where the estimated frequency-domain transfer function has a determinable value; and converting the determined frequency to an equivalent z-domain value.

14. The method of claim 13, further comprising:
determining the calibration coefficient based equivalent z-domain value and the determined values for the parameters of the estimated z-domain transfer function.

15. The method of claim 12, wherein defining the estimated z-domain transfer function comprises defining a polynomial numerator and a polynomial denominator for the estimated z-domain transfer function having the form:

$$H_{IO}(z) = \frac{\sum_{n=1}^{N_b} b_n z^{-(n-1)}}{1 + \sum_{n=1}^{N_a} a_n z^{-n}}$$

where the polynomial numerator has order $N_b-1$, the denominator has order $N_a$, and the plurality of parameters are the coefficients $a_n$ and $b_n$.

16. The method of claim 1, further comprising calibrating a second uncalibrated sensor to the time-varying physical phenomenon at the first location to obtain the calibrated sensor, such that the second uncalibrated sensor, once calibrated, can be used as the calibrated sensor.

17. The method of claim 16, wherein calibrating the second uncalibrated sensor to the time-varying physical phenomenon at the first location comprises:
obtaining values of the input waveform of the time-varying physical phenomenon at the first location at at least a first time and a second time;
obtaining values of a second output waveform output by the second uncalibrated sensor corresponding to the time-varying physical phenomenon at the first location at at least the first time and the second time;
determining a second calibration coefficient for the second uncalibrated sensor for the time-varying physical phenomenon at the first location based on the obtained values for at least the first time and the second time of the input and second output waveforms; and
determining a second calibration constant for the second uncalibrated sensor based on the determined second calibration constant, the input waveform and the second output waveform, wherein the determined second calibration coefficient and the determined second calibration constant calibrate the second uncalibrated sensor to the time-varying physical phenomenon at the first location.

18. A method for calibrating an electronic applanation tonometer, comprising:
measuring a brachial artery blood pressure with a calibrated oscillometric blood pressure monitor to generate a calibrated oscillometric blood pressure signal;
measuring a radial artery blood pressure with an uncalibrated electronic applanation tonometer to generate a voltage signal;
determining a frequency-domain pressure-to-voltage transfer function based on the calibrated oscillometric blood pressure signal and the voltage signal of the uncalibrated electronic applanation tonometer;
determining a calibration coefficient for the uncalibrated electronic applanation tonometer based on frequency-domain pressure-to-voltage transfer function;
determining a calibration constant for the uncalibrated electronic applanation tonometer based on the determined calibration constant, the calibrated oscillometric blood pressure signal and the voltage signal, wherein the determined calibration coefficient and the determined calibration constant calibrate the uncalibrated electronic applanation tonometer to the radial artery blood pressure.

* * * * *